United States Patent [19]
Zeikus et al.

[11] Patent Number: 4,737,459
[45] Date of Patent: * Apr. 12, 1988

[54] REGULATION AND ENHANCEMENT OF ENZYME PRODUCTION

[75] Inventors: Joseph G. Zeikus, Okemos, Mich.; Hyung-Hwan Hyun, Seoul, Rep. of Korea

[73] Assignee: Michigan Biotechnology Institute, East Lansing, Mich.

[*] Notice: The portion of the term of this patent subsequent to Aug. 5, 2003 has been disclaimed.

[21] Appl. No.: 716,045

[22] Filed: Mar. 26, 1985

Related U.S. Application Data

[63] Continuation-in-part of Ser. No. 652,585, Sep. 18, 1984, Pat. No. 4,647,538, and a continuation-in-part of Ser. No. 652,586, Sep. 18, 1984, Pat. No. 4,628,031, and a continuation-in-part of Ser. No. 652,588, Sep. 18, 1984, Pat. No. 4,604,352.

[51] Int. Cl.$^4$ .................. C12N 9/34; C12N 9/44; C12N 9/22; C12P 7/14
[52] U.S. Cl. .................. 435/162; 435/205; 435/210; 435/200; 435/42; 435/842
[58] Field of Search ............. 435/42, 95, 98, 161, 435/162, 172, 201, 210, 842

[56] References Cited

U.S. PATENT DOCUMENTS 4,604,352  8/1986  Zeikus et al. .................. 435/42
4,628,031  12/1986  Zeikus et al. .................. 435/205

FOREIGN PATENT DOCUMENTS 0088656  9/1983  European Pat. Off. ......... 435/172.1

OTHER PUBLICATIONS

VanUden et al., Selective "Isolation of Derepressed Mutants of an β-Amylase Yeast by the Use of 2-Deoxyglucose".
Biotechnology & Bioengineering, vol. 22, pp. 651–654, (1980), Chem. Abstract, vol. 99, 1983, p. 532, #211183u, Monique et al., "Production of Mutants of C, Acetolatylicum, with High Productivity of Butanol and Acetone.
Zeikus, J. G., A. Ben–Bassat, and P. Hegge, 1980, Microbiology of Methanogenesis in Thermal, Volcanic Environments, J. Bact. 143: 432–440.
Schink, B., and J. G. Zeikus, 1983, *Clostridium Thermosulfurogenes* sp. nov., a New Thermophile that Produces Elemental Sulfur from Thiosulphate, J. Gen. Microbiol. 129: 1149–1158.
Hyun, H. H., J. G. Zeikus, R. Longin, J. Millet, and A. Ryter, 1983, Ultrastructure and Extreme Heat Resistance of Spores from Thermophilic Clostridia, J. Bact. 156: 1332–1337.
Matteuzzi, D., F. Hollaus, and B. Biavati, 1978, Proposal of Neotype for *Clostridium Thermohydrosulfuricum* and the Merging of *Clostridium Tartarivorum* with *Clostridium Thermosaccharolyticum*, Int. J. System, Bacteriol, 28: 528–531.
Lovitt, R. W., R. Longin, and J. G. Zeikus, 1984, Ethanol Production by Thermophilic Bacteria: Physiological Comparison of Solvent Effects on Parent and Alcohol–Tolerant Strains of *Clostridium Thermohydrosulfuricum*, Appl. Environ. Microbiol, 48, 171–177.

(List continued on next page.)

Primary Examiner—John E. Tarcza
Attorney, Agent, or Firm—Quarles & Brady

[57] ABSTRACT

A method is disclosed for producing catabolite repression-resistant mutant strains of *C. thermosulfurogenes* and *C. thermohydrosulfuricum*. The method comprises challenging a wild strain of the organism with nitrosoguanidine, followed by enrichment on 2-deoxyglucose and culturing an iodine stained starch-glucose containing agar. The colonies which convert starch most efficiently are catabolite repression-resistant. Pure cultures of the mutants and methods employing the mutants to prepare enzymes are also described.

2 Claims, 4 Drawing Sheets

OTHER PUBLICATIONS

Zeikus, J. G., 1983, Metabolic Communication Between Biodegradative Populations in Nature, In: Microbs in Their Natural Environments, J. H. Slater, R. Whittenbury and J. W. T. Wimpenny, (eds.), Symposium 34 Society for General Microbiology Ltd., Cambridge University Press, 1983.

Zeikus, J. G. and T. K. Ng, 1982, Thermophilic Saccharide Fermentations in: *Annual Report of Fermentation Processes*, G. Tsao, Editor, vol. 5, 7: 263–289.

Ng. T. K., A. Ben-Bassat, and J. G. Zeikus, 1981, Ethanol Production by Thermophilic Bacteria: Fermentation of Cellulosic Substrates by Co-Cultures of *Clostridium Thermocellum* and *Clostridium Thermohydrosulfuricum*, Appl. Environ. Microbiol. 41: 1337–1343.

Zeikus, J. G., 1979, Thermophilic Bacteria: Ecology, Physiology, and Technology, Enzyme Microb. Technol. 1: 243–252.

REGULATION AND ENHANCEMENT OF ENZYME PRODUCTION

RELATED CASE

This is a continuation-in-part of our copending earlier application Ser. Nos. 652,585, now U.S. Pat. No. 4,647,538; 652,586, now U.S. Pat. No. 4,628,031, and 652,588, now U.S. Pat. No. 4,604,352, all filed on Sept. 18, 1984.

FIELD OF THE INVENTION

The present invention relates to the production of enzymes. More particularly, it relates to the production of thermostable enzymes and ethanol by catabolite repression-resistant mutant strains of microorganisms.

BACKGROUND OF THE INVENTION

There is an active interest in the production of industrial feedstock chemicals or fuels from biomass. Starch is a major component of agricultural crops and of corn processing waste and it is a preferred substrate for chemical and enzyme production because of its chemical composition and its higher density than other forms of biomass which facilitates prolonged storage, and decreases transportation and pretreatment costs.

Starch is known to be a valuable starting material for the enzymatic production of sugar, such as glucose, which may be converted by yeast to ethanol. The main amylolytic or starch converting enzymes used for the industrial production of glucose, maltose and maltosaccharide from starch are $\alpha$-amylase, $\beta$-amylase, glucoamylase and pullulanase.

The known amylolytic enzymes, except for bacterial $\alpha$-amylases, are unstable at the elevated temperatures preferred for the industrial conversion of starch.

In our earlier U.S. patent application Ser. Nos. 652,585; 652,586 and 652,588, all filed Sept. 18, 1984 we disclosed the preparation of thermostable $\beta$-amylase; the preparation of thermostable glucoamylase and pullulanase and the co-culture production of those enzymes and ethanol, respectively.

Although the microbial strains disclosed in our earlier applications produce the thermostable enzymes in useful quantities, it would obviously be desirable to have mutant strains that result in a more efficient method of converting starch into ethanol and greater production of thermostable enzymes.

BRIEF SUMMARY OF THE INVENTION

One object of the present invention is to disclose a method for developing mutant strains which produce greater quantities of thermostable starch converting enzymes.

It is a further object to disclose pure cultures of the more productive novel mutant strains.

It is a still further object to disclose more efficient methods of producing ethanol directly from starch and also producing thermostable starch converting enzymes using the novel mutant strains.

We have discovered that novel catabolite repression-resistant mutant strains of *Clostridium thermosulfurogenes* and *Clostridium thermohydrosulfuricum* which produce higher quantities of thermostable enzymes than the wild strains can be obtained by challenging the wild strains with N-methyl-N-nitro-N-nitrosoguanidine and followed by enrichment in the presence of 2-deoxyglucose.

Using the above described method we have obtained several mutant strains that produce larger amounts of desired enzymes than the parent or wild strain. For example, we have produced a novel mutant strain of *C. thermosulfurogenes* which produces 8 times as much $\beta$-amylase on starch medium than the wild type. In addition, the mutant strain more rapidly ferments starch to ethanol than the wild strain.

We also have produced novel mutants of *C. thermohydrosulfuricum* which produce twice as much glucoamylase and pullulanase as the wild strain and which display improved starch metabolism.

We also have discovered an improved, single step method for the production of both ethanol and thermostable starch converting enzymes which comprises culturing co-cultures of the novel mutants of *Clostridium thermosulfurogenes* and *Clostridium thermohydrosulfuricum* under anaerobic conditions on a growth medium containing starch and essential minerals, vitamins and growth factors until detectable enzymatic activity and/or ethanol are present and then, if desired, isolating the enzymes and/or ethanol.

The foregoing objects and other advantages are accomplished by the present invention which is further described in the drawings and the description of the preferred embodiment.

DESCRIPTION OF PREFERRED EMBODIMENT

Figure 1:
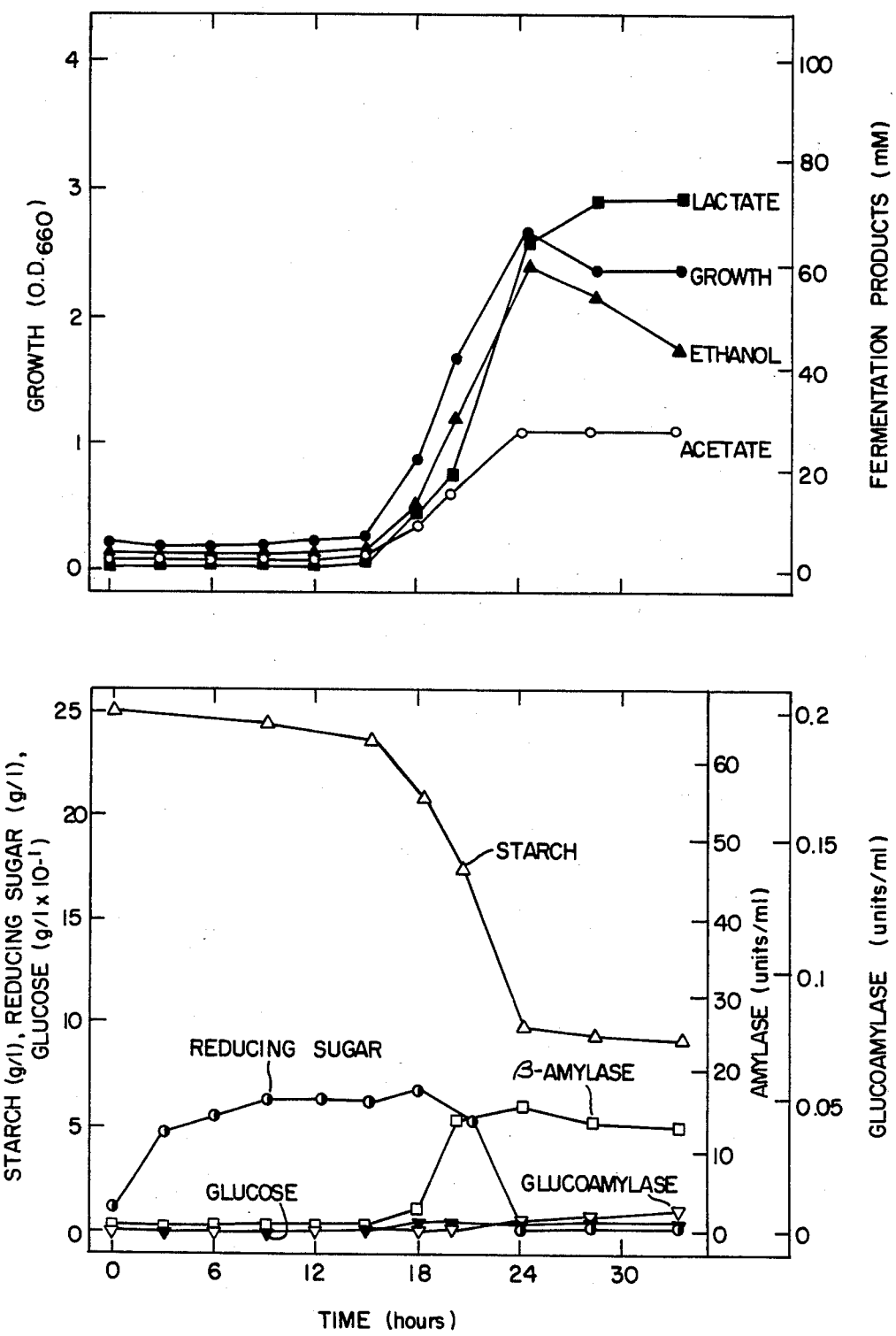
FIG. 1. Shows the starch metabolism time course of *C. thermosulfurogenes* wild type strain in a gassed, pH-controlled fermenter. Experiments were conducted in a fermenter that contained 650 ml TYE medium and 2.5% starch, which was continuously gassed with $N_2/CO_2$ (95:5), and controlled at pH 7.0.

In one embodiment of the present invention novel catabolite repression-resistant mutant strains of *Clostridium thermosulfurogenes* strain 4B (ATCC 33743) are obtained by growing cultures of the organism in TYEG medium until the mid logarithmic growth stage followed by centrifugation and suspension in fresh TYEG medium, they are treated with N-methyl-N'-nitro-N-nitrosoguanidine to produce a cell viability loss of greater than 99%. The treated cells were washed with reduced LPBM medium, suspended in TYEG medium, and incubated. The cells were washed again with reduced LPBM medium to remove glucose, and then suspended in TYE medium that contained starch and 2-deoxyglucose. After incubation the cells were plated on TYE agar medium containing starch and glucose and incubated. The plates were replica-plated in an anaerobic chamber onto TYEG agar medium, and the replica plates were incubated. The host plates were flooded with iodine solution, and the colonies with large clear zones on the iodine-stained plates were selected as the catabolite repression-resistant mutants from the replica plates by contrasting the colony position of the host and replica plates. For isolation of constitutive mutants, the replica plates were again replica-plated onto TYEG agar medium. The second replica plates were incubated. The first replica plates were flooded with starch-agar solution in 0.1M sodium acetate buffer (pH 6.0), the incubated, and iodine-stained. The colonies with large clear zones on the iodine-stained plates were selected as the constitutive mutants from the second replica plates.

In a second embodiment of the present invention novel catabolite repression-resistant mutant strains of Clostridium thermohydrosulfuricum wild type (ATCC No. 33223) were prepared in the manner described above.

The practice of the invention is further described in the experimental reports which follow:

Preparation of Novel Mutant Strains of C. thermosulfurogenes

MATERIALS AND METHODS

Chemicals and gases. All chemicals were reagent grade and were obtained from either Mallinkrodt (Paris, KY) or Sigma Chemical Co. (St. Louis, MO). All gases were obtained from Matheson (Joliet, IL) and were purified free of oxygen by passage over heated (370° C.) copper filings.

Organisms and cultivation conditions. C. thermosulfurogenes strain 4B was isolated from Octopus Spring algalbacterial mat in Yellowstone National Park and maintained by anoxic and stringent aseptic culture techniques. Experimental cultures were grown at 60° C. without shaking in 125 ml Wheaton serum bottles or in anaerobic pressure tubes (Bellco Glass, Inc., Vineland, NJ) that contained 50 ml or 10 ml, respectively, of TYE medium with the fermentable carbon sources indicated, and a $N_2/CO_2$ (95:5) gas headspace. Culture medium was autoclaved for 45 min. to ensure destruction of the extremely heat resistant spores of thermoanaerobes. Starch metabolism time course studies on 2.5% starch were conducted in a New Brunswick Multigen Fermenter (New Brunswick Scientific Co., Edison, NJ) that contained 650 ml of the modified TYE medium. The TYE medium was modified to contain the double strengths of vitamin solution, ammonium chloride, magnesium chloride and trace mineral solution. The fermenters were mixed at 200 rpm, gassed continuously with $N_2/CO_2$ (95:5) at a flow rate of 200 ml per min., and controlled at pH 6.0 with 1.7N ammonium hydroxide solution.

Continuous cultures were conducted in a New Brunswick Multigen Fermenter with 320 ml of working volume that was mixed at 200 rpm, and continuously gassed with $N_2/CO_2$ (95:5) at a flow rate of 40 ml per min. without pH control. The continuous culture was initiated by introducing TYE medium with 0.4% carbon source into the fermenter from the reservoir after an inoculum was grown in the vessel to the logarithmic growth phase. For isolation of pure cultures, the organism was streaked onto plates of TYE medium that contained 0.5% starch and 3.0% purified agar (Difco, Detroit, MI) in an anaerobic chamber (Coy Laboratory Products, Ann Arbor, MI). The plates were placed into an anoxic paint can (W. R. Brown Division Intermatic, Spring Grove, IL) under nitrogen and incubated for 4 days at 60° C. C. thermosulfurogenes wild type strain 4B (ATCC 33743) and mutant strain H12-1 (ATCC 53034) was deposited in American Type Culture Collection, Rockville, MD.

Mutagenesis, enrichment, and isolation of mutants. The following procedures were performed using anaerobic techniques. The cultures grown on TYEG medium until the mid logarithmic growth phase ($O.D._{660}=0.5$) were centrifuged, suspended in fresh TYEG medium, and then treated with N-methyl-N'-nitro-N-nitrosoguanidine (250 $\mu$-NTG/ml) at 60° C. for 1 hour. NTG treatment resulted in cell viability loss of greater than 99%. The treated cells were washed twice with reduced LPBM medium, suspended in TYEG medium, and incubated at 60° C. for 7 hours. The cells were washed three times with reduced LPBM medium to remove glucose, and then suspended in TYE medium that contained 0.5% starch and 0.05% 2-deoxyglucose. After incubation at 60° C. for 20 hours, the cells were plated on TYE agar medium containing 0.5% starch and 1.5% glucose and incubated at 60° C. for 4 days. The plates were replicaplated in an anaerobic chamber onto TYEG agar medium, and the replica plates were incubated for 4 days. The host plates were flooded with iodine solution (1 g $I_2$ and 2 g KI per 300 ml $H_2O$), and the colonies with large clear zones on the iodine-stained plates were selected as catabolite repression-resistant mutants from the replica plates by contrasting the colony position of the host and replica plates. For isolation of constitutive mutants, the replica plates were again replica-plated onto TYEG agar medium. The second replica plates were incubated at 60° C. for 4 days. The first replica plates were flooded with starch (2%)-agar (3%) solution in 0.1M sodium acetate buffer (pH 6.0), then incubated at 60° C. for 8 hours, and iodine-stained. The colonies with large clear zones on the iodine-stained plates were selected as constitutive mutants from the second replica plates.

Quantification of growth, fermentation substrates and end products. Culture turbidities were directly determined by inserting anaerobic pressure tubes into a Spectronic 20 spectrophotometer (Bausch and Lomb, Rochester, NY). In starch metabolism time course studies, culture broths were diluted 5 times with double distilled water to measure optical density. Cell dry weight was determined by filtration of fermentation broths through 0.45 $\mu$m filter (Millipore Corp., Bedford, MA), washing once with double distilled water, and drying at 65° C. until constant weights were obtained.

To measure starch concentration, the culture broth samples were appropriately diluted with water and 50 $\mu$l of sulfuric acid solution (5M) was added to 0.5 ml samples. These samples were placed in a steam bath for 3 hours and then neutralized by the addition of 35 $\mu$l sodium hydroxide solution (10N). The starch concentration was estimated by fitting the reducing sugar values to the calibration curve for starch solutions which were treated by the same procedures as above.

Glucose was enzymatically determined by the hexokinase and glucose-6-phosphate dehydrogenase method. Reducing sugar was estimated using glucose as a standard by the dinitrosalicylic acid method. Total carbohydrates were assayed by the phenol-sulfuric acid method. The levels of sucrose or maltose in carbon-limited chemostats also were detected by the phenol-sulfuric acid method. Ethanol and acetate were measured by gas chromatography using a flame ionization detector. L-lactic acid was assayed by standard procedures using lactic dehydrogenase. Hydrogen was quantified by thermal conductivity detection. $CO_2$ production was calculated by the sum of ethanol and acetate production.

Enzyme assays. Cell-free culture broth and washed cells were prepared by centrifugation of culture broths at 10,000×g for 10 min. The precipitated cells were suspended in the appropriate amount of double distilled water. The cell-free broth and cell suspensions were used for measurement of β-amylase and glucoamylase activities, respectively. For measurement of glucose isomerase activity, culture broths were anaerobically centrifuged in $N_2$-gassed centrifugal tubes. The precipitated cells were suspended in 2 μM $MgCl_2$ solution that was gassed with $N_2$ and reduced with 2 μM dithiothreitol.

β-Amylase activity was assayed in reaction mixtures (5 ml) that consisted of 2% soluble starch in 0.1M sodium acetate buffer (pH 6.0) and the appropriately diluted enzyme. After aerobic incubation at 60° C. for 30 min., the reaction was stopped by cooling on ice. The released reducing sugar was measured by the dinitrosalicylic acid method. One unit of β-amylase activity is defined as the amount of enzyme that released 1 μmol of reducing sugar as a glucose standard per min. under the assay conditions.

Glucoamylase activity was measured in reaction mixtures that consisted of 0.5 ml of 2% soluble starch in 0.2M sodium acetate buffer (pH 4.8) and 0.5 ml of enzyme solution. After aerobic incubation at 60° C. for 30 min., the reaction was stopped by cooling on ice, and then it was boiled in a steam bath for 10 min. The released glucose was quantified using the hexokinase and glucose-6-phosphate dehydrogenase method. One unit of glucoamylase activity is defined as the amount of enzyme that liberated one μmol of glucose per min. under the assay conditions.

Glucose isomerase activity was anaerobically assayed in $N_2$-gassed anaerobic pressure tubes that contained 10 ml of reaction mixture. The reaction mixture consisted of 50 mM phosphate buffer (pH 7.0), 25% D-glucose, 50 mM $MgSO_4$, 0.5 mM $CoCl_2$, 0.3% Triton X-100, 2 mM dithiothreitol, and the enzyme source. After incubation at 60° C. for one hour with shaking, the reaction was stopped by the addition of 20 μl of perchloric acid (2M). The released fructose was quantified by the cysteine-carbazole method. One unit of glucose isomerase activity is defined as the amount of enzyme that produced 1 μmol of D-fructose per min. under the assay conditions.

RESULTS

Relation of β-amylase production to carbon sources. The effects of various sugars on β-amylase formation are shown in Table 1. The data indicated that β-amylase of *C. thermosulfurogenes* is only expressed in high levels when cells are grown on maltose or other carbohydrates containing maltobiose units as inducers for enzyme synthesis. Table 2 shows the effect of maltose on expression of β-amylase in the presence of various carbon growth substrates. β-Amylase production was severely repressed by glucose but not by sucrose, cellobiose of fructose. These findings suggest that β-amylase synthesis in this species may be regulated by induction and catabolite repression mechanisms.

Isolation of regulatory mutants. Experimental techniques for isolation of regulatory mutants were based on the assumption that β-amylase production was regulated by induction and catabolite repression. Table 3 shows the effect of 2-deoxyglucose, a known non-metabolizable catabolite repressor, on growth of *C. thermosulfurogenes*. The organism did not grow in 20 hours on starch medium with higher than 0.005% of 2-deoxyglucose or on 2-deoxyglucose alone but grew on glucose medium with 2-deoxyglucose. The reason for growth at longer incubation times may be related to low levels of amylase synthesis under catabolite repression. Therefore, 2-deoxyglucose was used as a non-metabolizable catabolite repressor for enrichment of catabolite-repression-resistant mutants.

According to experimental procedures described in Materials and Methods section, about 700 colonies were isolated and tested for alteration in the regulatory nature of β-amylase production. Three major kinds of mutants were further purified and characterized. The β-amylase activities of wild type and mutant strains grown on various carbon sources are compared in Table 4. The mutants were confirmed to be stable by testing for β-amylase productivities after at least 10 culture transfers. The mutant H35 produced about 3-fold more β-amylase on starch medium than the wild type; and, upon the addition of glucose to starch medium, it still produced high activity of β-amylase but not on glucose medium alone. Therefore, it was classified as a catabolite repression-resistant but inducible mutant. In contrast, mutant H227-7 was classified as constitutive strain because it produced 3-fold more β-amylase regardless of growth substrates than the wild type on starch medium. The mutant H12-1 produced 8-fold more β-amylase on starch medium than the wild type but its β-amylase productivity was significantly increased by the presence of starch. Therefore, it was classified as a hyperproductive mutant being both constitutive and catabolite repression-resistant.

Induced synthesis of β-amylase. Dependence of the differential rate of β-amylase synthesis on the concentration of maltose was compared in the wild type, catabolite repression-resistant but inducible mutant H35, and constitutive and catabolite repression-resistant mutant H12-1 (FIG. 1). The data indicate that maltose is required as an inducer for expression of β-amylase in this species because in the wild type and mutant H35, β-amylase was only produced upon the addition of maltose to the cells growing on sucrose medium, whereas the differential rate of β-amylase synthesis by constitutive mutant H12-1 was almost constant regardless of the presence of maltose.

In order to eliminate the possibility of regulation of β-amylase synthesis by repression (i.e., constitutive but catabolite repressible), carbon-limited chemostat studies were performed. Under carbon-limited growth conditions, both wild type and mutant H35 produced β-amylase only on maltose as a sole carbon source but not on glucose or sucrose (Table 5). Therefore, it was concluded that β-amylase production is regulated by induction and catabolite repression in this species.

Catabolite repression of β-amylase synthesis.

Figure 2A:
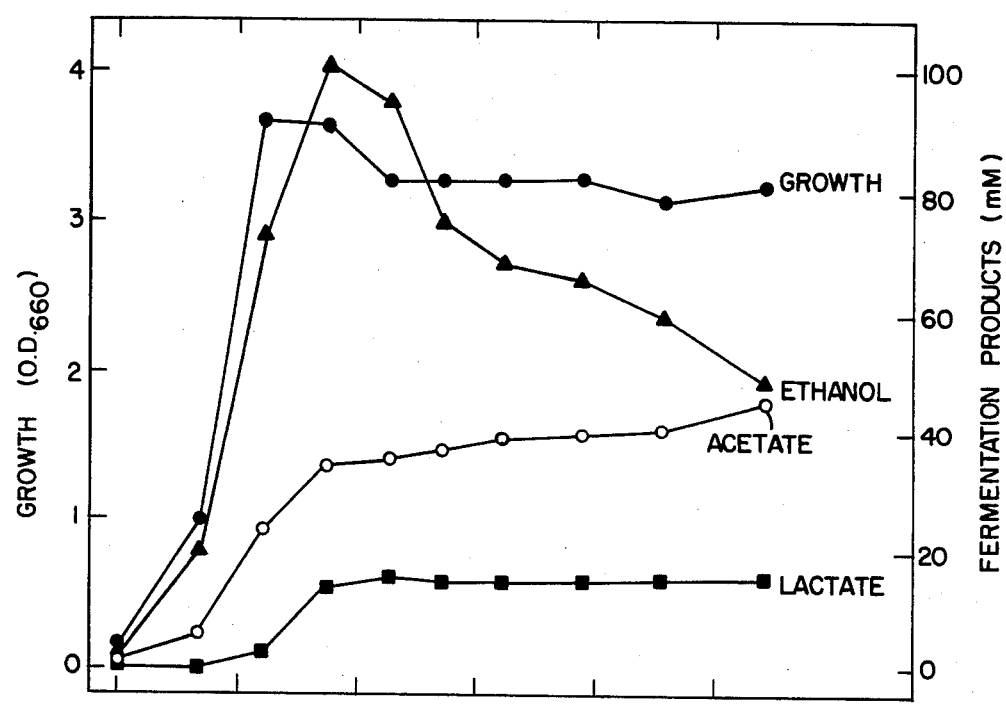
FIG. 2. Shows the starch metabolism time course of *C. thermosulfurogenes* mutant strain H12-1 in a gassed, pH controlled fermenter. Experimental procedures were same as in FIG. 1.
Figure 2B:
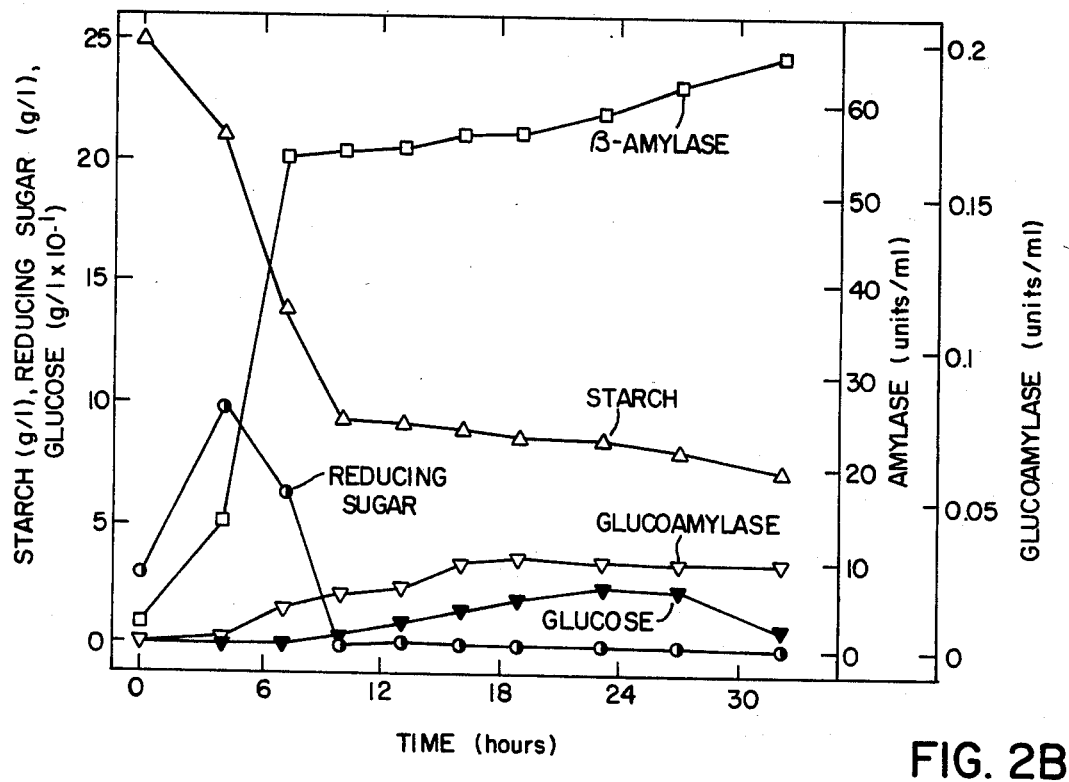

FIG. 2 shows the effects of glucose on cAMP on the differential rate of β-amylase synthesis by *C. thermosulfurogenes* wild type and mutant H35. β-Amylase formation in the wild type strain was immediately repressed by the addition of 0.5% glucose to the cells growing on maltose, whereas in the catabolite repression-resistant mutant H35, it was entirely not affected. Also, the simultaneous addition of 5 or 10 mM of cAMP with 0.5% glucose to the growing culture of wild type strain did not relieve the catabolite repression by the glucose (FIG. 2A). These observations suggest that β-amylase synthesis in the wild type strain is subject to catabolite repression.

Effects of antibiotics addition on subsequent secretion of β-amylase. The addition of rifampicin (100 μg/ml) or tetracycline (100 μg/ml), inhibitory to ribonucleic acid or protein synthesis, to the wild type strain culture which was actively secreting β-amylase caused an immediate cessation of further enzyme production. These results indicate that the secretion of β-amylase in this species involves de novo synthesis rather than liberation or activation of preformed enzyme.

General characterization of mutants. The mutants were initially compared to the wild type in terms of morphological and physiological alterations. The mutants were different in morphology from the wild type in TYEG medium, and consisted of single or paired cells instead of the long filamentous chains of cells displayed by the wild type. In addition, the mutants were altered in the ability to transform thiosulphate to elemental sulphur but not in sporulation (Table 6). The constitutive mutant (H12-1) did not grow on starch medium containing 0.5% thiosulphate but the catabolite repression-resistant mutant (H35) grew with a long lag time (more than 2 days) but the growth yield was low. In a view of end product formation pattern, the 3 mutants produced more ethanol than the wild type as a result of switching from lactate to ethanol production (Table 7). It is also notable that the constitutive mutants, H227-7 and H12-1 grew more rapidly on starch medium than the wild type. Therefore, these facts indicate that these mutants were altered regulationally in β-amylase production as well as metabolically.

In order to investigate whether the mutants were altered specifically in β-amylase production alone or also in the production of other saccharide transforming enzymes, glucoamylase and glucose isomerase activities were compared in the wild type and mutants grown on various substrates (Table 8). The data indicate that the mutants (H35 and H12-1) were not constitutive for general enzyme production whereas, they were catabolite repression-resistant for both β-amylase and glucoamylase production but not for glucose isomerase production. These observations suggest that the mutants were altered specifically for regulation of amylolytic enzyme synthesis.

Comparison of starch metabolism time course. Experiments were performed to assess the potential improvement of constitutive mutants for industrial application in starch transformation processes. FIG. 1 and FIG. 2 compare the fermentation time course of C. thermosulfurogenes wild type and constitutive mutant H12-1, respectively, grown on 2.5% starch under conditions of continuous gassing and pH control at 6.0. The data show that starch metabolism was significantly improved in mutant compared to the wild type in terms of total metabolic rate and amylase production. The mutant produced about 4 fold more β-amylase (66 units/ml) than the wild type (16 units/ml), and displayed the higher metabolic rate in terms of growth, starch consumption and end product formation. It is also notable that the mutant produced more ethanol and less lactate than the wild type. The decrease of ethanol concentration observed during the stationary growth phase was the result of evaporation caused by gassing.

DISCUSSION

In general, these results prove that amylase synthesis is regulated and is a rate limiting step during growth of thermoanaerobes on starch. Furthermore, techniques were developed to obtain regulatory mutants which enhance the overall starch metabolism physiology of C. thermosulfurogenes.

The data demonstrate that β-amylase synthesis in C. thermosulfurogenes is regulated by induction and catabolite repression, and that the appearance of β-amylase in the culture medium of this species has the characteristics of de novo synthesis during the period of secretion. β-Amylase synthesis in Bacillus is well studied, and depending on species is constitutive and catabolite repressible, inducible and catabolite repressible, or partially constitutive. However, the regulation mechanism of β-amylase synthesis in microorganisms is not known to our knowledge. We also demonstrated that the synthesis of glucoamylase and pullulanase in Clostridium thermohydrosulfuricum was inducible and subject to catabolite repression. Therefore, these findings advance the fundamental understanding of the regulation mechanism of saccharolytic enzyme synthesis in thermoanaerobic bacteria.

The failure of cAMP to relieve β-amylase secretion from the catabolite repression by glucose may be due to cellular impermeability of C. thermosulfurogenes to the molecules or a different specific regulation mechanism. Starch itself is too large to enter the cell, and therefore maltose derived from starch by extracellular β-amylase that is formed in trace amounts under non-induced states may serve as a natural inducer. The data showed that mutants H35 and H12-1 were catabolite repression-resistant for synthesis of amylase but not for synthesis of glucose isomerase. Also, the β-amylase hyperproductive mutant H12-1 was not constitutive for synthesis of enzymes other than β-amylase.

Notably, hyperproductive mutant H12-1 as compared to the wild type, produced up to 8 times the amount of β-amylase produced by the wild type strain; displayed a faster metabolic rate in terms of growth rate, starch consumption rate and ethanol production rate; and, produced more ethanol in relation to the decreased production of lactate. Previously, we discovered and disclosed in our copending patent applications that C. thermosulfurogenes β-amylase has the practical potential for production of maltose from starch because it is more thermostable and active than the plant β-amylase which is used in starch processing industries, and moreover that it can be used in combination with pullulanase of C. thermohydrosulfuricum which is extremely thermostable and active at nearly the same pH and temperature range as the β-amylase. Also, we have discovered a co-culture process for production of amylase (β-amylase, glucoamylase and pullulanase) and ethanol in a single step starch fermentation.

In view of the fact that both enzyme and ethanol yields need to be improved for practical applications of thermoanaerobes in starch fermentations, the hyperproductive mutant H12-1 which is both constitutive and catabolite repression-resistant has greater industrial potential for production of thermostable enzymes and ethanol than the wild type strain. Mutant H12-1 produces the highest activity of β-amylase among the known microbial or plant β-amylase producers.

TABLE 1

Effect of Carbon Sources on Extracellular β-Amylase Production by *Clostridium thermosulfurogenes*[a]

| Growth Substrate | Final Cell Concentration (O.D.$_{660}$) | Doubling Time (hrs) | β-Amylase (units/ml) |
|---|---|---|---|
| Glucose | 1.40 | 1.2 | 0.0 |
| Xylose | 1.35 | 1.5 | 0.1 |
| Mannose | 1.35 | 1.4 | 0.1 |
| Fructose | 1.30 | 1.5 | 0.6 |
| Sucrose | 1.20 | 1.9 | 0.1 |
| Cellobiose | 1.38 | 1.3 | 0.0 |
| Maltose | 1.10 | 1.9 | 6.4 |
| Maltotriose | 1.10 | 1.8 | 8.0 |
| Amylose | 0.73 | 1.3 | 3.1 |
| Amylopectin | 0.80 | 1.4 | 6.7 |
| Soluble Starch | 0.95 | 1.7 | 6.0 |
| Insoluble Starch | 0.95 | — | 4.9 |
| Glycogen | 0.95 | 1.3 | 6.6 |

[a]Cells were cultivated in pressure tubes containing TYE medium plus 0.5% of each substrate at 60° C. and harvested at about 2 hrs into stationary phase. Cultures pre-grown in a medium containing the carbon course indicated were used as the inoculum source.

TABLE 2

Comparison of β-Amylase Activity in Relation to the Utilization of Various Saccharides in the Presence or Absence of Maltose as Carbon Sources for Growth of *C. thermosulfurogenes*[a]

| Substrates | Growth (O.D.$_{660}$) | β-Amylase Activity (units/ml) |
|---|---|---|
| Maltose | 1.30 | 6.0 |
| Glucose | 1.45 | 0.2 |
| Glucose + Maltose | 1.20 | 0.1 |
| Xylose | 1.45 | 0.2 |
| Xylose + Maltose | 1.50 | 1.4 |
| Fructose | 1.60 | 0.2 |
| Fructose + Maltose | 1.60 | 2.0 |
| Mannose | 1.60 | 0.1 |
| Mannose + Maltose | 1.60 | 1.3 |
| Cellobiose | 1.45 | 0.2 |
| Cellobiose + Maltose | 1.38 | 3.3 |
| Sucrose | 1.25 | 0.2 |
| Sucrose + Maltose | 1.30 | 4.1 |

[a]Cultures pre-grown on TYEG medium were washed three times with reduced LPBM medium and were then used as inoculum. Supernatants were assayed for β-amylase activity from cultures grown at 60° C. for 30 hours without shaking in pressure tubes containing 10 ml of TYE medium with carbon sources as indicated. The concentration of maltose and other saccharides was 0.5% and 1.5%, respectively.

TABLE 3

Effect of 2-Deoxyglucose Concentration on the Growth of *C. thermosulfurogenes* with Glucose or Starch as Carbon Source[a]

| 2-Deoxyglucose Concentration (%) | Growth (O.D.$_{660}$) 20 Hr | 30 Hr |
|---|---|---|
| Controls | | |
| No carbon source | 0.125 | 0.14 |
| 0.5% 2-deoxyglucose alone | 0.06 | 0.084 |
| Starch | | |
| 0 | 0.88 | 0.86 |
| 0.5 | 0.06 | 0.09 |
| 0.05 | 0.07 | 0.31 |
| 0.005 | 0.08 | 0.46 |
| 0.0005 | 0.88 | 1.05 |
| Glucose | | |
| 0 | 1.05 | 1.20 |
| 0.5 | 0.61 | 0.70 |
| 0.05 | 1.08 | 1.25 |

[a]Cells were cultivated in pressure tubes containing LPBM medium with 0.3% yeast extract, 0.5% glucose or starch, and various concentrations of 2-deoxyglucose without shaking at 60° C.

TABLE 4

Comparison of β-Amylase Activities in *C. thermosulfurogenes* Wild Type and Mutant Strains[a]

| Strain | Growth Substrate | Growth (O.D.$_{660}$) | β-Amylase (U/ml) |
|---|---|---|---|
| Wild type | 1% Starch | 1.30 | 6.0 |
|  | 0.5% Starch + 1.5% Glucose | 1.30 | 1.6 |
|  | 1% Sucrose | 1.30 | 0.2 |
|  | 1% Glucose | 1.10 | 0.2 |
| Catabolite Repression-Resistant Mutant | | | |
| H35 | 1% Starch | 1.30 | 16.2 |
|  | 0.5% Starch + 1.5% Glucose | 1.30 | 10.8 |
|  | 1% Sucrose | 1.35 | 0.4 |
|  | 1% Glucose | 1.28 | 0.1 |
| Constitutive, Catabolite-Repression Resistant Mutants | | | |
| H227-7 | 1% Starch | 1.55 | 20.7 |
|  | 0.5% Starch + 1.5% Glucose | 1.15 | 18.5 |
|  | 1% Sucrose | 1.30 | 15.6 |
|  | 1% Glucose | 1.28 | 18.0 |
| Hyperproductive Mutant | | | |
| H12-1 | 1% Starch | 1.40 | 46.3 |
|  | 0.5% Starch + 1.5% Glucose | 1.40 | 34.6 |
|  | 1% Sucrose | 1.40 | 18.8 |
|  | 1% Glucose | 1.45 | 16.0 |

[a]Cells were cultivated in pressure tubes containing 10 ml of TYE medium with carbohydrates as indicated, at 60° C. for 20 hours without shaking.

TABLE 5

β-Amylase Activities in Wild Type and Catabolite Repression Resistant Mutant Strains of *C. thermosulfurogenes* Grown in Carbon Source-Limited Chemostats[a] 282

| Strain | Carbon Source | Dilution Rate (Hr$^{-1}$) | Cell Conc. (O.D.$_{660}$) | β-Amylase (U/ml) |
|---|---|---|---|---|
| Wild Type | Glucose | 0.20 | 1.08 | 0.37 |
|  |  | 0.40 | 1.08 | 0.35 |
|  | Sucrose | 0.18 | 1.00 | 0.32 |
|  |  | 0.36 | 1.12 | 0.26 |
|  | Maltose | 0.18 | 1.12 | 13.2 |
|  |  | 0.36 | 1.15 | 13.0 |
| Mutant H35 | Glucose | 0.22 | 1.00 | 0.35 |
|  |  | 0.40 | 1.04 | 0.36 |
|  | Sucrose | 0.18 | 1.12 | 0.29 |
|  |  | 0.36 | 1.12 | 0.26 |
|  | Maltose | 0.18 | 1.10 | 13.7 |
|  |  | 0.36 | 1.18 | 13.8 |

[a]Growth limiting conditions were established by using 0.4% of carbon source concentration in a reservoir. Carbon-limited growth conditions were confirmed by the facts that the addition of carbon source to the fermentor caused increase of cell concentration and C-source was non-detectable by the assay procedures as described in the experimental method section. Chemostats were operated at 60° C. and were continuously gassed with $N_2/CO_2$ (95:5).

TABLE 6

Comparison of Growth, Thiosulfate Transformation and Sporulation in Mutant and Wild Type Strains of *C. thermosulfurogenes*[a]

| Strain | Thiosulfate Addition | Growth Lag | (O.D.$_{660}$) | Thiosulfate Transformation | Sporulation |
|---|---|---|---|---|---|
| Wild Type | — | 0 | 1.30 | + | + |
|  | + | 0 | 1.40 |  |  |
| H35 | — | 0 | 1.30 | + | + |
|  | + | >2 days | 0.62 |  |  |
| H12-1 | — | 0 | 1.40 | — | + |
|  | + | No Growth |  |  |  |

[a]Experiments were conducted in a pressure tube that contained 10 ml of TYE medium with 1% starch and with/without 0.5% thiosulfate for thiosulfate transformation studies, and that contained 10 ml of LPBM medium with 0.2% xylose plus 0.05% yeast extract for sporulation studies. Sporulation ability was determined by phase microscopic examination of the cultures grown on the sporulatin medium. Thiosulphate transformatin in elemental sulfur was determined by the procedures of Schink and Zeikus (24).

TABLE 7

Comparison of Growth and Fermentation Product Formation by Wild Type and Mutant Strains of *C. thermosulfurogenes*[a]

| Strain | Growth Substrate | Growth (O.D.$_{660}$) | $\mu$max (hr$^{-1}$) | Substrate Consumption ($\mu$mol as glucose) | End Product ($\mu$mol/tube) | | | | |
|---|---|---|---|---|---|---|---|---|---|
| | | | | | Ethanol | Acetate | Lactate | H$_2$ | CO$_2$ |
| Wild Type | Glucose | 1.20 | 0.55 | 278 | 245 | 136 | 180 | 288 | 381 |
| | Maltose | 1.04 | 0.36 | 270 | 300 | 154 | 140 | 331 | 454 |
| | Starch | 0.93 | 0.41 | 185 | 246 | 116 | 7 | 270 | 362 |
| H35 | Glucose | 1.20 | 0.47 | 278 | 454 | 111 | 74 | 248 | 565 |
| | Maltose | 1.25 | 0.30 | 287 | 427 | 94 | 54 | 336 | 521 |
| | Starch | 1.00 | 0.40 | 203 | 268 | 104 | 4 | 270 | 372 |
| H227-7 | Glucose | 1.10 | 0.58 | 278 | 436 | 143 | 33 | 337 | 579 |
| | Maltose | 1.40 | 0.34 | 286 | 399 | 125 | 90 | 348 | 524 |
| | Starch | 1.05 | 0.52 | 198 | 244 | 114 | 0 | 275 | 358 |
| H12-1 | Glucose | 1.35 | 0.52 | 278 | 420 | 138 | 10 | 365 | 558 |
| | Maltose | 1.25 | 0.33 | 284 | 430 | 120 | 20 | 329 | 550 |
| | Starch | 1.05 | 0.52 | 187 | 299 | 100 | 0 | 243 | 399 |

[a]Cells were cultivated in a pressure tube containing 10 ml of TYE medium plus 0.5% of each substrate at 60° C. without shaking for 20 hrs.

TABLE 8

Comparison of Saccharide Transforming Enzyme Activities in Wild Type and Mutant Strains of *C. thermosulfurogenes*[a]

| Strain-Growth Conditions | Growth | $\beta$-Amylase (U/ml) | Glucoamylase (U/ml) | Glucose Isomerase (U/ml) |
|---|---|---|---|---|
| Wild type | | | | |
| 1% Starch | 1.30 | 6.0 | 0.006 | — |
| 0.5% Starch + 1.5% Glucose | 1.30 | 1.6 | 0.000 | — |
| 0.5% Glucose | 1.08 | 0.2 | 0.000 | 0.02 |
| 0.5% Xylose | 1.00 | — | — | 0.28 |
| 0.5% Xylose + 1.5% Glucose | 1.30 | — | — | 0.02 |
| Catabolite Repression-Resistant Mutant H35 | | | | |
| 1% Starch | 1.30 | 16.2 | 0.009 | — |
| 0.5% Starch + 1.5% Glucose | 1.35 | 10.8 | 0.002 | — |
| 0.5% Glucose | 1.10 | 0.1 | 0.000 | 0.02 |
| 0.5% Xylose | 1.00 | — | — | 0.27 |
| 0.5% Xylose + 1.5% Glucose | 1.30 | — | — | 0.02 |
| Constitutive and Catabolite Repression Resistant Mutant H12-1 | | | | |
| 1% Starch | 1.35 | 46.3 | 0.009 | — |
| 0.5% Starch | 1.40 | 34.6 | 0.011 | — |
| 0.5% Glucose | 1.10 | 16.0 | 0.000 | 0.02 |
| 0.5% Xylose | 0.95 | — | — | 0.27 |
| 0.5% Xylose + 1.5% Glucose | 1.30 | — | — | 0.03 |

[a]Enzyme activities were measured as described in Materials and Methods after growth under the conditions stated.

Preparation of Novel Mutant Strains of *C. thermohydrosulfuricum*

MATERIALS AND METHODS

Chemical and gases. All chemicals were reagent grade and were obtained from either Mallinkrodt (Paris, KY) or Sigma Chemical Co. (St. Louis, MO). All gases were obtained from Matheson (Joliet, IL) and were purified free of oxygen by passage over heated (370° C.) copper filings.

Organisms and cultivation conditions. *C. thermohydrosulfuricum* strain 39E was isolated from Octopus Spring in Yellowstone National Park, and maintained by anoxic and stringent aseptic culture techniques. Experimental cultures were grown at 65° C. without shaking in 125 ml Wheaton bottles or in 26 ML anaerobic pressure tubes (Bellco Glass Co., Vineland, NJ) that contained 50 ml or 10 ml, respectively, of TYE medium with the fermentable carbon sources indicated, and an N$_2$ (95:5) gas headspace. Culture media were autoclaved for 45 minutes to assure killing the extremely heat resistant spores. Starch metabolism time course studies were conducted in a New Brunswick Multigen Fermenter (New Brunswick Scientific Co., Edison, NJ) that contained 650 ml of the modified TYE medium and 2.5% soluble starch. The medium was modified to contain the double strengths of vitamin solution, ammonium chloride, magnesium chloride, and trace mineral solution. The fermenters were mixed at 200 rpm, gassed continuously with N$_2$/CO$_2$ (95:5) at a flow rate of 200 ml per min, and controlled at pH 6.0 with 1.7 ammonium hydroxide solution. Chemostat studies were conducted in a New Brunswick Multigen Fermenter with 320 ml of working volume that was mixed at 200 rpm, and continuously gassed with N$_2$/CO$_2$ (95:5) at a flow rate of 40 ml per min without pH-control. After an inoculum was grown in the vessels to the logarithmic growth phase, the continuous culture was initiated when a TYE medium containing 0.4% of carbon sources indicated was introduced into the fermenter vessel from the reservoir.

For isolation of pure cultures, the organism was streaked onto plates of TYE medium that contained 0.5% starch and 3.0% purified agar (Difco, Detroit, MI) in an anaerobic chamber (Coy Products, Ann Arbor, MI). The plates were placed into an anoxic paint can (W. R. Brown Division Intermatic, Spring Grove, IL) under nitrogen and incubated for 4 days. *C. thermohydrosulfuricum* wild type (ATCC 33223) and mutant strain Z21-109 (ATCC 53033) were deposited in the American Type Culture Collection, Rockville MD.

Mutagenesis, enrichment and isolation of mutants. Cultures grown on TYEG medium until the mid logarithmic growth phase ($O.D._{660}=0.5$) were centrifuged, suspended in fresh TYEG medium, and treated with N-methyl-N-nitrosoguanidine (400 μg-NTG/ml at 65° C. for 1 hour. NTG-treatment resulted in cell viability loss of greater than 99%. The treated cells were washed twice with reduced LPBM medium, suspended in TYEG medium, and incubated for 8 hours. The cells were washed three times with reduced LPBM medium to remove glucose, then suspended in TYE medium containing 0.5% starch and 0.05% 2-deoxyglucose, and incubated at 65° C. for 20 hours. The cells were plated onto TYE gear medium containing 1.5% glucose and 0.5% starch in anaerobic chamber, and then incubated at 60° C. for 4 days. The host plates were flooded with iodine solution (1 g $I_2$ and 2 g KI per 300 ml), and the colonies displaying large clear zones on the iodine-stained plates were selected as catabolite repression-resistant mutants from replica plates by contrasting the colony position of the host and replica plates.

Growth and metabolic characterization. Culture turbidities were determined by inserting anaerobic pressure tubes into a Spectronic 20 spectrophotometer (Bausch and Lomb, Rochester, NY). In starch metabolism time course studies, culture broths were diluted 5 times with double distilled water to measure optical density. Cell dry weight was determined by filtration of fermentation broths through 0.45 μm filter (Millipore Corp., Bedford, MA), washing once with double distilled water, and drying at 65° C. until constant weights were obtained.

Sporulation ability was tested by phase-microscopic examination of the spore suspension prepared according to the procedures described previously. Thiosulfate transformation into hydrogen sulfide was determined by the appearance of black precipitates upon the addition of ferric chloride solution (100 mM) to the culture broths grown on TYEG medium containing 0.5% thiosulphate.

To measure starch concentration, the culture broth samples were appropriately diluted with water, and 50 μl of sulfuric acid solution (5M) was added to 0.5 ml samples. These samples were placed in a steam bath for 3 hours and then neutralized by the addition of 35 μl sodium hydroxide solution (10N). The starch concentration was estimated by fitting the reducing sugar values to the calibration curve for starch solutions which were treated by the same procedures as above. Glucose was determined by the hexokinase and glucose-6-phosphate dehydrogenase method. Reducing sugar was estimated using glucose as a standard by the dinitrosalicylic acid method. Total carbohydrates were assayed by the phenol-sulfuric acid method. The levels of xylose and starch in carbon-limited chemostats also were detected by the phenol-sulfuric acid method.

Ethanol and acetate were measured by gas chromatography using a flame ionization detector. L-lactic acid was assayed by standard procedures using lactic dehydrogenase. Hydrogen was quantified by thermal conductivity detection. $CO_2$ production was calculated as the sum of ethanol and acetate production.

Enzyme assays. Cell extracts or cell suspensions were used for determination of enzyme activities. For determination of amylolytic enzyme activities, cell suspensions were prepared by centrifugation of culture broths at $10,000 \times g$ for 10 min, and the precipitated cells were suspended in the appropriate amount of double distilled water. For determination of glucose isomerase activity, culture broths were anaerobically centrifuged in $N_2$-gassed centrifugal tubes, and the precipitated cells were suspended in 2 mM $MgCl_2$ solution that was gassed with $N_2$ and reduced with 2 mM dithiothreitol. Cell extracts were prepared by passage of the cell suspensions through a French pressure cell at 20,000 lb/in$^2$. The supernatant was collected by centrifugation at $30,000 \times g$ for 30 min at 4° C. and was used for analysis of amylase activities. Protein concentration was determined by Lowry method (19).

Pullulanase activity was measured by incubating a reaction mixture (1 ml) that consisted of 1% pullulan in 0.1M sodium acetate buffer (pH 6.0) and the enzyme source at 60° C. for 30 min. The reaction was stopped by immersing the reaction tubes in an ice bath and adding 4 ml of the cooled 3,5-dinitrosalicylic acid. One unit of pullulanase activity is defined as the amount of enzyme which liberated 1 μmol of reducing sugar with glucose as a standard per min under the described conditions. Glucoamylase, isomaltase and lactase activities were measured in reaction mixtures (1 ml) that consisted of 1% soluble starch, 1% isomaltose and 2% lactose, respectively in 0.1M sodium acetate buffer (pH 4.8), and the enzyme source. After incubating at 60° C. for 30 min, the reaction mixtures were boiled in a steam bath for 10 min, and centrifuged to remove the insoluble materials. The released glucose was estimated by the hexokinase and glucose-6-phosphate dehydrogenase method. One unit of glucoamylase, isomaltase and lactase is defined as the amount of enzyme that produced one μmol of glucose per min under the assay conditions. Glucose isomerase activity was anaerobically measured in $N_2$-gassed anaerobic pressure tubes that contained 10 ml of reaction mixtures. The reaction mixtures consisted of 25% D-glucose, 50 mM $MgSO_4$ 0.5 mM $CoCl_2$, 0.3% Triton X-100, 2 mM dithiothreitol, 50 mM Trishydrochloride buffer (pH 8.55), and the enzyme source. After incubation at 60° C. for 2 hours with reciprocal shaking, the reaction was stopped by the addition of 20 μl of 2M perchloric acid. The released D-fructose was quantified by the cysteine-carbazole method. One unit of glucose isomerase activity is defined as the amount of enzyme that isomerized 1 μmol of glucose into fructose per min under the assay conditions.

RESULTS

Relation of glucoamylase and pullulanase production to carbon sources. Table 9 shows that glucoamylase and pullulanase are only detected when cells are grown on stimulatory substrates such as maltose or other carbohydrates containing maltobiose units. Further experiments were initiated to test whether enzyme production was regulated. Table 10 shows the effects of maltose on expression of glucoamylase and pullulanase by *C. thermohydrosulfuricum* in medium with various carbon sources as a growth substrate. These results indicate that both glucoamylase and pullulanase production are more severely repressed by glucose than xylose or lactose. These findings suggest that amylase production may be regulated by induction and catabolite repression in this species.

Isolation of catabolite repression resistant mutants. These studies were initiated in order to confirm the assumption made about regulation of glucoamylase and pullulanase synthesis. Table 11 shows that 2-deoxyglucose served as a non-metabolizable catabolite repressor in *C. thermohydrosulfuricum* because the species grew on glucose medium with 2-deoxyglucose but not on starch medium with higher than 0.005% of 2-deoxyglucose or on 2-deoxyglucose alone. Therefore, mutants were isolated through mutagenesis with NTG, enrichment using 2-deoxyglucose, and selection of colonies with large halos on starch-glucose agar plates that were stained with iodine. About 800 colonies were tested for alteration in the regulational nature of enzyme synthesis and 2 major kinds of mutants were chosen and further characterized. The glucoamylase and pullulanase activities of wild type and mutant strains grown on various carbon sources are compared in Table 12. These mutants were confirmed to be stable by testing amylase productivities after at least 10 culture transfers on various carbon sources. The data show that both mutants Z67-143 and Z21-109 were catabolite repression resistant because they produced the same amount of glucoamylase and pullulanase on starch (0.5%) medium with glucose (1.5%) as produced by the wild type on starch (1%) medium. Notably the mutants, Z21-109 produced about two fold more amylases on starch medium than the wild type and it was classified as a hyperproductive mutant.

Induced synthesis and catabolite repression of amylase synthesis. The effect of starch concentration on the diffential rate of amylase synthesis was compared in the wild type and mutant strain Z21-109. The data indicate that inducer (e.g., starch) is required for expression of both pullulanase and glucoamylase because in both wild type and mutant strain, the enzymes were only synthesized upon the addition of starch to the cells growing on xylose. It is notable that the differential rate of enzyme synthesis decreased during the logarithmic growth phase for both activities according to the increase of starch concentration in the wild type but not in the mutant, due to the catabolite repression caused by glucose accumulation from the action of glucoamylase and pullulanase during starch fermentation.

In order to eliminate the possibility of regulation of amylase synthesis by repression (i.e., constitutive but catabolite repressible), carbon-limited chemostat studies were performed. Table 13 shows that both glucoamylase and pullulanase were expressed by both wild type and mutant Z21-109 in starch-limited chemostat cultures but not in glucose- or xylose-limited conditions. It is also notable that both glucoamylase and pullulanase activities in starch-limited chemostats were significantly higher as compared to that obtained from batch cultures on starch medium (Table 12) indicating catabolite repression by glucose which accumulated from the action of glucoamylase and pullulanase during the batch starch fermentation time course.

General characterization of mutants. The mutants were similar to the wild type in morphology, thiosulphate transformation into hydrogen sulfide, and sporulation. Table 14 shows that the mutants displayed higher growth rate and yield on starch medium than the wild type, due to the enhanced amylase activities and also to a less extent from improved resistance to lysis in the stationary phase. It is notable that mutant Z21-109 produces more ethanol than the wild type as a consequence of decreased lactate production. Other experiments were performed in order to investigate whether the catabolite repression-resistant mutants were altered specifically in glucoamylase and pullulanase production alone or also in the production of other saccharide transforming enzymes. Table 15 indicates the mutant Z21-109 is catabolite repression resistant for various saccharide transforming enzymes in addition to glucoamylase and pullulanase because it produced glucose isomerase, isomaltase and lactase under the conditions that repressed enzyme synthesis in the wild type.

Figure 3A:
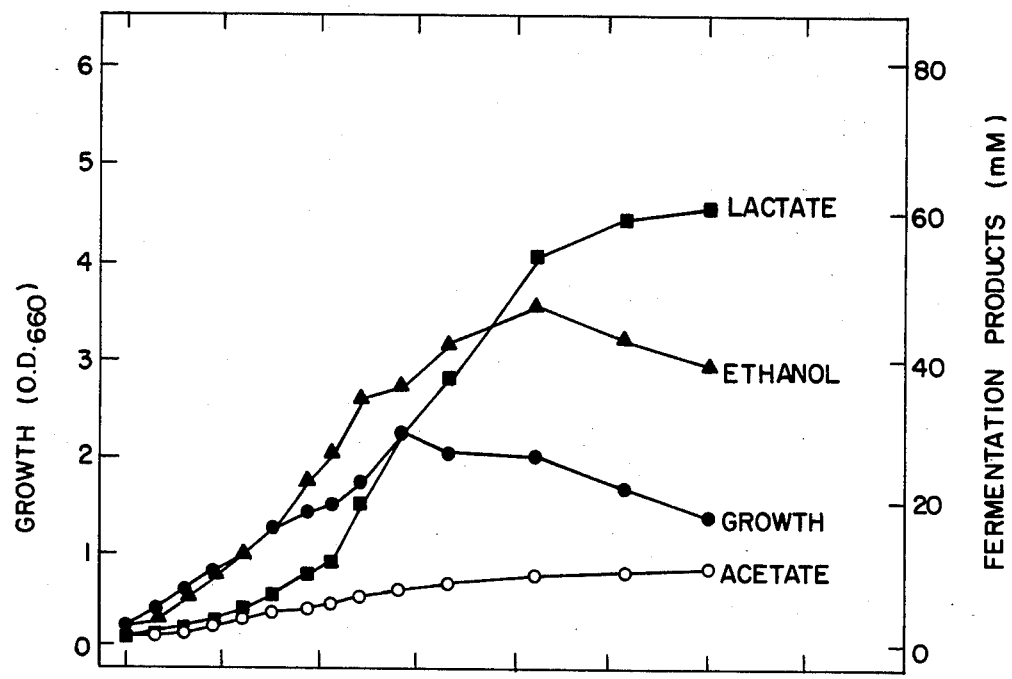
FIG. 3. Shows the starch metabolism time course of *C. thermohydrosulfuricum* wild type strain 39E in a gassed, pH-controlled fermenter. Experiments were conducted in a fermentor containing 650 ml of TYE medium and 2.5% soluble starch, which was continuously gassed with $N_2/CO_2$ (95:5) and controlled at pH 7.0.
Figure 3B:
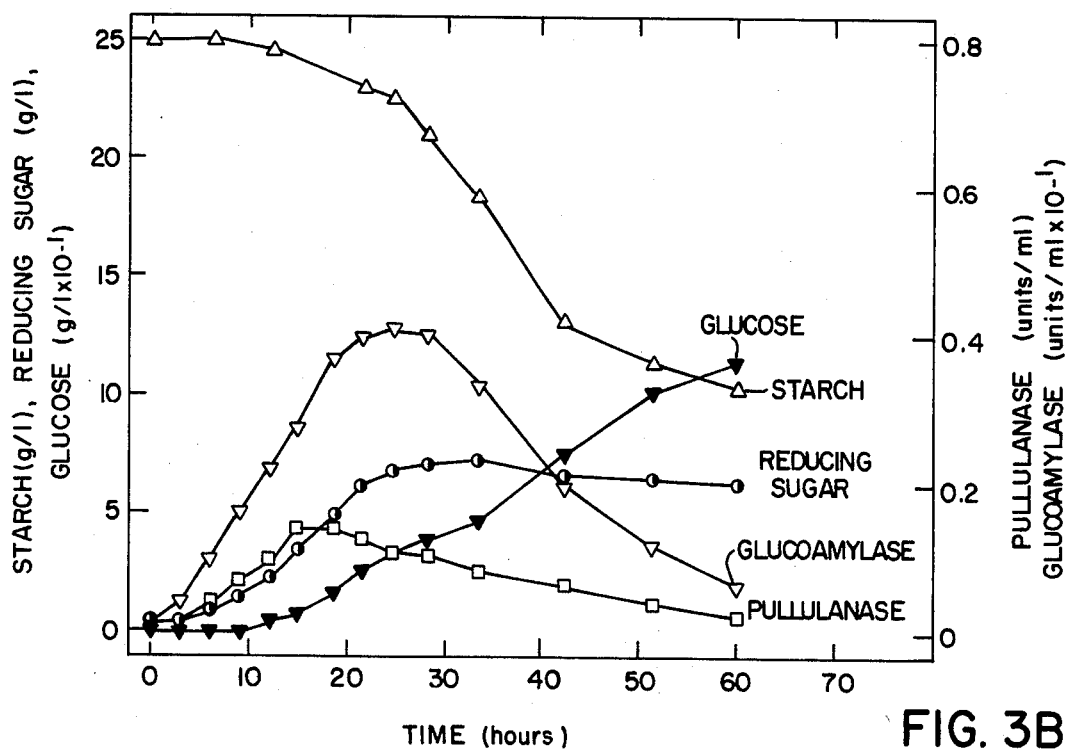
Figure 4A:
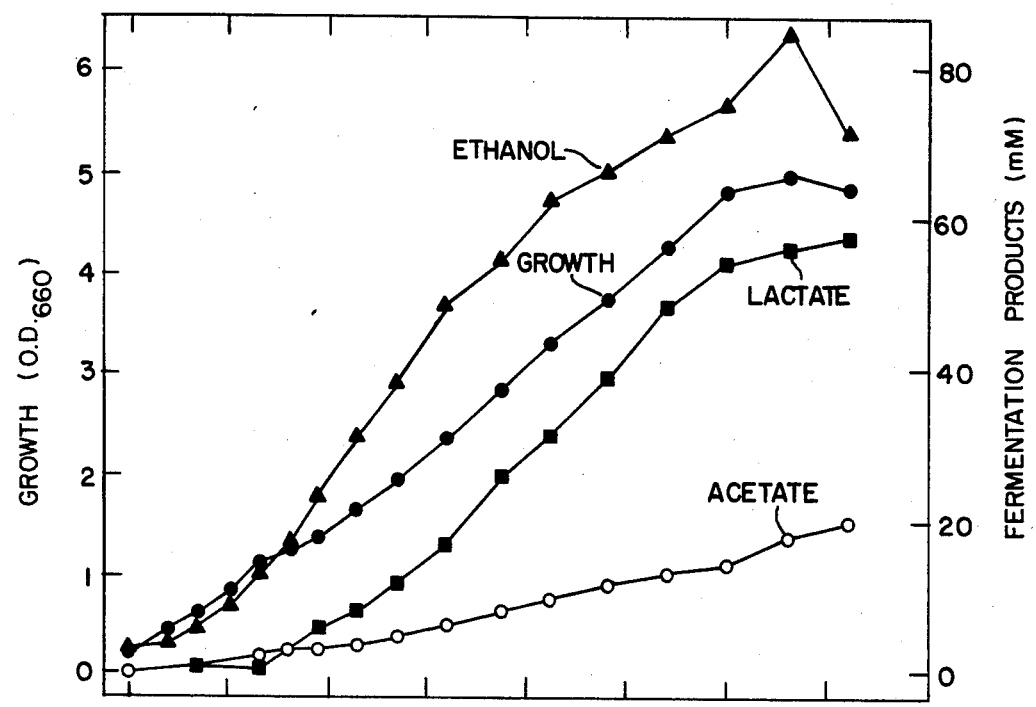
FIG. 4. Shows the starch metabolism time course of *C. thermohydrosulfuricum* mutant strain Z21-109 in a gassed, pH-controlled fermenter. Experimental procedures were same as in FIG. 3.
Figure 4B:
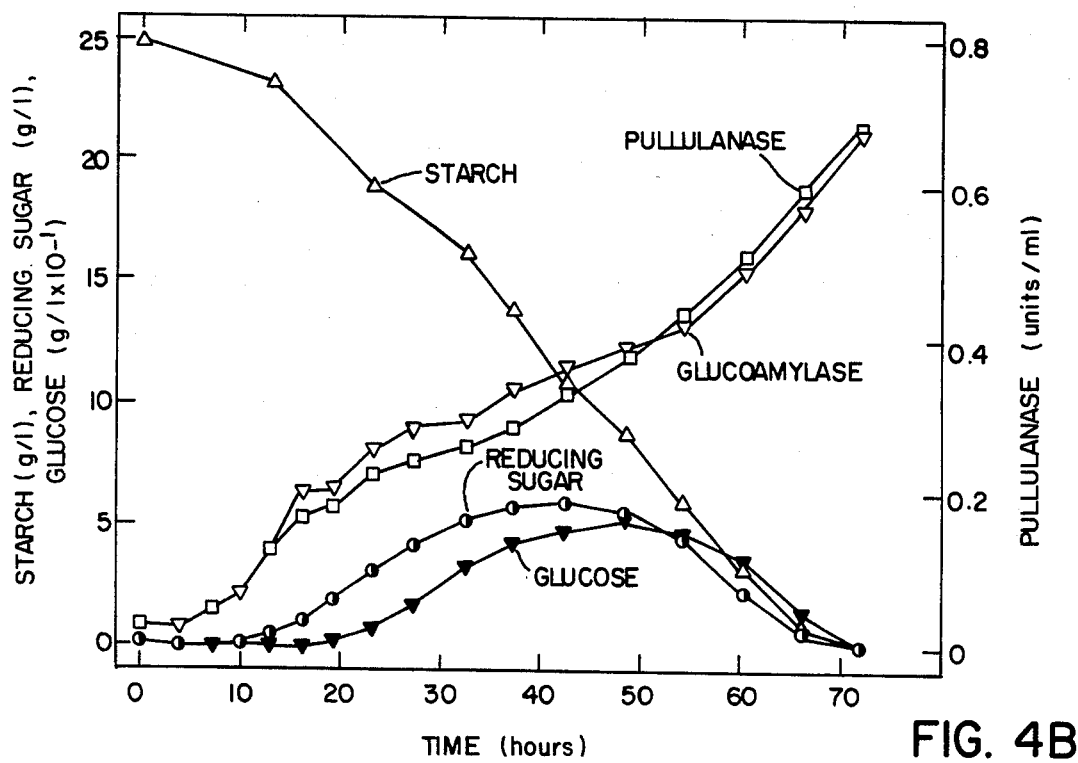

Comparison of starch metabolism time courses in wild type and hyperproductive mutant strains. This study was performed to assess both catabolite repression resistance and the potential improvement of mutants for industrial applications in starch transformation processes. FIGS. 3 and 4 compare the fermentation time course of *C. thermohydrosulfuricum* wild type and mutant Z21-109, respectively, grown on 2.5% starch under conditions of continuous gassing and pH control at 6.0. In the wild type strain, starch was not completely utilized under the conditions employed. Reducing sugar and glucose accumulated continuously during the entire culture period. Growth and end product formation nearly ceased, even in the presence of large quantities of reducing sugar and glucose in the medium, and this was followed by decrease in glucoamylase and pullulanase activities due to extensive cell lysis. On the other hand, in mutant strain, starch metabolism was significantly improved compared to the wild type in terms of starch utilization, amylase production and ethanol production. Growth of the mutant continued until starch was completely utilized. Reducing sugar and glucose accumulation increasd in the early growth phase and disappeared at the end of fermentation. Notably, the mutant produced more ethanol and amylase. The decrease of ethanol concentration observed during the stationary growth phase was the result of evaporation caused by gassing.

DISCUSSION

In general, these results prove that amylase synthesis is regulated and is a rate limiting step during growth of thermoanaerobes on starch. Furthermore, techniques were developed to obtain hyperproductive, catabolite repression resistant amylase mutants which enhanced the overall starch metabolism physiology of *C. thermohydrosulfuricum*.

The data demonstrate that glucoamylase and pullulanase synthesis is induced by maltose and other carbohydrates containing maltose units, and subject to catabolite repression in *C. thermohydrosulfuricum*. In this regard, we have also found that synthesis of extracellular $\beta$-amylase in *C. thermosulfurogenes* is regulated by an induction and catabolite repression mechanism. Essentially, nothing is known about the regulation mechanisms for saccharidase synthesis in thermophiles or anaerobes. Therefore, the findings here advance the fundamental understanding of regulational mechanisms involved in saccharide fermentations by these poorly studied microbes. These data also help, in part, to explain the basis for enhancement of glucoamylase and pullulanase activities by co-cultures between *C. thermohydrosulfuricum* and *C. thermosulfurogenes*. The catabolite repression caused by glucose accumulation during starch fermentation of *C. thermohydrosulfuricum* was eliminated by the consumption of glucose by both species in co-culture.

The mutants obtained here displayed faster growth rate and yield, and higher yields of ethanol and amylases in relation to complete utilization of starch (2.5%) as compared to the wild type. Recently, ethanol-resistant mutants were isolated in *Clostridium thermocellum* and *C. thermohydrosulfuricum*. However, isolation of mutants with regulational alteration in saccharidase production was never reported previously in obligate thermophiles or anaerobes. We have also isolated constitutive or derepressed mutants of *C. thermosulfurogenes* in β-amylase production. The β-amylase constitutive mutant produced 8 fold more β-amylase on starch medium than the wild type, and also it produced more ethanol due to switching from lactate to ethanol production.

We previously demonstrated that glucoamylase and pullulanase of *C. thermohydrosulfuricum* and β-amylase of *C. thermosulfurogenes* were extremely thermostable and thermoactive. Therefore, achievement of strain improvements with amylase mutants suggests that a genetic approach is feasible to advance the practical potential of using thermoanaerobic fermentations for industrial production of amylases as well as ethanol from starch.

TABLE 9

Effect of Carbon Sources on Production of Amylases by *Clostridium thermohydrosulfurogenes*[a]

| Growth Substrate | Final Cell Concentration (O.D.$_{660}$) | Amylase Activity (unit/mg protein) Pullulanase | Glucoamylase |
|---|---|---|---|
| Glucose | 1.15 | 0.00 | 0.000 |
| Xylose | 0.98 | 0.00 | 0.000 |
| Mannose | 0.48 | 0.00 | 0.000 |
| Fructose | 0.63 | 0.00 | 0.000 |
| Cellobiose | 0.75 | 0.00 | 0.000 |
| Lactose | 0.56 | 0.00 | 0.000 |
| Maltose | 0.52 | 0.40 | 0.040 |
| Maltotriose | 0.59 | 0.36 | 0.041 |
| Amylopectin | 0.62 | 0.27 | 0.040 |
| Soluble Starch | 0.80 | 0.27 | 0.041 |
| Insoluble Starch | 0.46 | 0.18 | 0.030 |
| Glycogen | 0.66 | 0.37 | 0.040 |
| Pullulan | 0.24 | 0.51 | 0.030 |

[a]Cells were grown at 65° C. for 24 hrs in serum bottles containing 50 ml of TYE medium plus 0.5% of each substrate. Cultures pregrown in a medium containing the carbon source indicated were used as the inoculum source. Activities were measured in cell extracts.

TABLE 10

Comparison of Amylolytic Enzyme Activities in Relation to the Saccharide Composition of Growth Medium for *C. thermohydrosulfuricum*[a]

| Substrates | Growth (O.D.$_{660}$) | Amylase Activity (U/ml) Pullulanase | Glucoamylase |
|---|---|---|---|
| Maltose | 0.57 | 0.048 | 0.0104 |
| Glucose | 1.60 | 0.000 | 0.0001 |
| Glucose + Maltose | 1.60 | 0.000 | 0.0005 |
| Xylose | 1.08 | 0.001 | 0.0000 |
| Xylose + Maltose | 1.45 | 0.002 | 0.0049 |
| Fructose | 1.60 | 0.000 | 0.0000 |
| Fructose + Maltose | 1.60 | 0.000 | 0.0001 |
| Mannose | 1.58 | 0.000 | 0.0001 |
| Mannose + Maltose | 1.48 | 0.000 | 0.0001 |
| Cellobiose | 1.49 | 0.000 | 0.0000 |
| Cellobiose + Maltose | 1.45 | 0.001 | 0.0009 |
| Lactose | 1.40 | 0.000 | 0.0001 |
| Lactose + Maltose | 1.40 | 0.002 | 0.0035 |

[a]Cultures pregrown on TYEG medium were washed three times with reduced LPBM medium and used as inoculum. Cultures were grown without shaking in serum bottles containing 50 ml of TYE medium at 65° C. for 30 hrs, and then were washed with water and assayed for amylolytic enzymes. The concentration of maltose and other saccharides was 0.5% and 1.5%, respectively.

TABLE 11

Effect of 2-Deoxyglucose Concentration on the Growth of *C. thermohydrosulfuricum* with Glucose or Starch as Carbon Source[a]

| 2-Deoxyglucose Concentration (%) | Growth (O.D.$_{660}$) 20 Hr | 30 Hr |
|---|---|---|
| Controls | | |
| No carbon source | 0.05 | 0.05 |
| 0.5% 2-deoxyglucose alone | 0.10 | 0.07 |
| Starch | | |
| 0 | 0.56 | 0.60 |
| 0.5 | 0.11 | 0.11 |
| 0.05 | 0.11 | 0.19 |
| 0.005 | 0.09 | 0.12 |
| 0.0005 | 0.52 | 0.59 |
| Glucose | | |
| 0 | 0.67 | 0.70 |
| 0.5 | 0.36 | 0.44 |
| 0.05 | 0.37 | 0.45 |
| 0.005 | 0.46 | 0.54 |
| 0.0005 | 0.63 | 0.68 |

[a]Cells were cultivated in pressure tubes containing LPBM medium with 0.3% yeast extract, 0.5% glucose or starch, and various concentrations of 2-deoxyglucose without shaking at 65° C.

TABLE 12

Comparison of Amylolytic Enzyme Activities in *C. thermohydrosulfuricum* Wild Type and Mutant Strains[a]

| Strain | Growth Substrates | Growth (O.D.$_{660}$) | Pullulanase (U/ml) | Glucoamylase (U/ml) |
|---|---|---|---|---|
| Wild Type | 1% Starch | 1.23 | 0.23 | 0.030 |
| | 0.5% Starch + 1.5% Glucose | 1.40 | 0.00 | 0.000 |
| | 1% Xylose (or Glucose) | 0.95 (1.05) | 0.00 | 0.000 |
| Catabolite Repression Resistant Mutant | | | | |
| Z67-143 | 1% Starch | 1.16 | 0.23 | 0.030 |
| | 0.5% Starch + 1.5% Glucose | 1.35 | 0.23 | 0.020 |
| | 1% Xylose (or Glucose) | 1.05 (1.07) | 0.00 | 0.000 |
| Hyperproductive Mutant | | | | |
| Z21-109 | 1% Starch | 1.30 | 0.43 | 0.048 |
| | 0.5% Starch + 1.5% Glucose | 1.30 | 0.24 | 0.026 |
| | 1% Xylose (or Glucose) | 0.95 (1.08) | 0.00 | 0.000 |

[a]Cells were cultivated in pressure tubes containing 10 ml of TYE medium with carbon sources as indicated, at 65° C. without shaking for 24 hours. Enzyme activities were measured in cell suspensions washed with water.

TABLE 13

Amylase Activities in Wild Type and Catabolite Repression Resistant Strains of *C. thermohydrosulfuricum* Grown in Carbon Source-Limited Chemostats[a]

| Strain | Carbon Source | Dilution Rate (hr$^{-1}$) | Cell Conc. (O.D.$_{660}$) | Glucoamylase (U/ml) | Pullulanase (U/ml) |
|---|---|---|---|---|---|
| Wild Type | Glucose | 0.04 | 0.98 | 0.000 | 0.00 |

TABLE 13-continued

Amylase Activities in Wild Type and Catabolite Repression Resistant Strains of *C. thermohydrosulfuricum* Grown in Carbon Source-Limited Chemostats[a]

| Strain | Carbon Source | Dilution Rate ($hr^{-1}$) | Cell Conc. ($O.D._{660}$) | Gluco-amylase (U/ml) | Pullu-lanase (U/ml) |
|---|---|---|---|---|---|
| | | 0.08 | 1.00 | 0.000 | 0.00 |
| | | 0.19 | 1.02 | 0.000 | 0.00 |
| | Xylose | 0.04 | 1.10 | 0.000 | 0.00 |
| | | 0.08 | 1.10 | 0.000 | 0.00 |
| | | 0.16 | 1.00 | 0.000 | 0.00 |
| | Starch | 0.11 | 1.10 | 0.059 | 0.31 |
| | | 0.17 | 1.10 | 0.043 | 0.34 |
| Mutant Z21-109 | Glucose | 0.08 | 1.02 | 0.000 | 0.00 |
| | | 0.19 | 1.05 | 0.000 | 0.00 |
| | Xylose | 0.08 | 1.00 | 0.000 | 0.00 |
| | | 0.12 | 0.98 | 0.000 | 0.00 |
| | Starch | 0.08 | 1.00 | 0.045 | 0.36 |
| | | 0.12 | 1.10 | 0.054 | 0.39 |

[a] Growth limiting conditions were established by using 0.4% of carbon source in the reservoir, which maintained the concentration of carbon sources in the vessel at non-detectable levels. Chemostats were run at 60° C. without pH control, and continuously gassed with $N_2/CO_2$ (95:5). Washed cells were used for assay of amylases.

TABLE 14

Comparison of Growth and Fermentation Products in *C. thermohydrosulfuricum* Wild Type and Mutant Strains[a]

| Strain | Growth Substrate | Growth ($O.D._{660}$) | $\mu$max ($Hr^{-1}$) | Substrate Consumption ($\mu$mol as glucose) | End Product ($\mu$mol/tube) | | | | |
|---|---|---|---|---|---|---|---|---|---|
| | | | | | Ethanol | Acetate | Lactate | $H_2$ | $CO_2$ |
| Wild Type | Glucose | 0.97 | 0.36 | 278 | 498 | 50 | 83 | 48 | 548 |
| | Starch | 0.80 | 0.17 | 270 | 461 | 26 | 54 | 39 | 487 |
| Catabolite Repression Resistant Mutant | | | | | | | | | |
| Z67-143 | Glucose | 0.39 | 0.36 | 139 | 306 | 43 | 48 | 28 | 349 |
| | Starch | 1.00 | 0.16 | 248 | 390 | 35 | 25 | 40 | 426 |
| Hyperproductive Mutant | | | | | | | | | |
| Z21-109 | Glucose | 1.40 | 0.37 | 278 | 551 | 27 | 47 | 34 | 578 |
| | Starch | 1.18 | 0.28 | 271 | 472 | 39 | 36 | 44 | 511 |

[a] Cells were cultivated in a pressure tube containing 10 ml of TYE medium plus 0.5% of each substrate at 65° C. without shaking for 24 hrs.

TABLE 15

Comparison of saccharide transforming enzyme activities in *C. thermohydrosulfuricum* wild type and mutant strain, Z21-109.[a]

| Enzymes and Growth Substrate | Sp. Activity (U/mg-cells) | |
|---|---|---|
| | Wild Type | Mutant Z21-109 |
| Glucose Isomerase | | |
| 0.5% Glucose | 0.05 | 0.05 |
| 0.5% Xylose | 0.45 | 0.42 |
| 0.5% Xylose + 1.5% Glucose | 0.05 | 0.21 |
| Isomaltase | | |
| 0.5% Glucose | 0.00 | 0.00 |
| 0.5% Isomaltose | 0.44 | 0.76 |
| 0.5% Isomaltose + 1.5% Glucose | 0.03 | 0.14 |
| Lactase | | |
| 0.5% Glucose | 0.03 | 0.12 |
| 0.5% Lactose | 1.46 | 1.67 |
| 0.5% Lactose + 1.5% Glucose | 0.18 | 1.33 |

[a] Cells were grown in serum bottles containing 50 ml of TYE medium and growth substrates indicated, at 60° C. for 24 hours without shaking. Only Glucose isomerase activity was assayed anaerobically.

The mutant strains of the present invention can be used for the production of thermostable enzymes. For example, a catabolite repression-resistant mutant strain of *C. thermohydrosulfuricum* can be grown under anaerobic conditions on a substrate of carbohydrate in a medium comprising essential vitamins, minerals and growth factors to produce superior amounts of a thermostable amylase and a thermostable pullulanase. In addition a mutant strain of *C. thermosulfurogenes* can be grown under similar conditions to produce a thermostable glucoamylase. Alternatively, a co-culture of a substantially pure culture of a catabolite repression-resistant mutant strain of *Clostridium thermosulfurogenes* and a substantially pure culture of a catabolite repression-resistant mutant strain of *Clostridium thermohydrosulfuricum* can be grown under anaerobic conditions on a carbohydrate substrate in a medium comprising essential vitamins, minerals and growth factors to produce a thermostable $\beta$-amylase, a thermostable glucoamylase, a thermostable pullulanase and ethanol. As a result, starch can be directly converted to ethanol by growing a co-culture of a catabolite repression-resistant mutant strain of *Clostridium thermosulfurogenes* and a catabolite repression-resistant mutant strain of *Clostridium thermohydrosulfuricum* under anaerobic conditions on starch.

We claim:

1. A method for the co-production of a thermostable $\beta$-amylase, a thermostable glucoamylase, a thermostable pullulanase and ethanol which comprises growing a co-culture of a catabolite repression-resistant mutant strain of *Clostridium thermosulfurogenes* and a catabolite repression-resistant mutant strain of *Clostridium thermohydrosulfuricum* under anaerobic conditions on a carbohydrate substrate in a medium comprising essential vitamins, minerals and growth factors and recovering the enzymes and ethanol.

2. A method for the direct conversion of starch to ethanol which comprises growing a co-culture of a catabolite repression-resistant mutant strain of *Clostridium thermosulfurogenes* and a catabolite repression-resistant mutant strain of *Clostridium thermohydrosulfuricum* under anaerobic conditions on a substrate of carbohydrate in a medium comprising essential vitamins, minerals and growth factors until detectable ethanol is present and then isolating the ethanol that forms.

* * * * *